United States Patent
Amorese et al.

(10) Patent No.: US 11,732,253 B2
(45) Date of Patent: Aug. 22, 2023

(54) REPURPOSING BEADS IN SAMPLE CLEANUP

(71) Applicant: Tecan Genomics, Inc., Redwood City, CA (US)

(72) Inventors: Douglas A. Amorese, Los Altos, CA (US); David Ruff, Redwood City, CA (US)

(73) Assignee: Tecan Genomics, Inc., Redwood City, CA (US)

(*) Notice: Subject to any disclaimer, the term of this patent is extended or adjusted under 35 U.S.C. 154(b) by 250 days.

(21) Appl. No.: 17/165,438

(22) Filed: Feb. 2, 2021

(65) Prior Publication Data

US 2021/0238585 A1  Aug. 5, 2021

Related U.S. Application Data

(60) Provisional application No. 62/969,358, filed on Feb. 3, 2020.

(51) Int. Cl.
*C12N 15/10* (2006.01)
*C12Q 1/6874* (2018.01)

(52) U.S. Cl.
CPC ..... *C12N 15/1013* (2013.01); *C12N 15/1096* (2013.01); *C12Q 1/6874* (2013.01)

(58) Field of Classification Search
None
See application file for complete search history.

(56) References Cited

U.S. PATENT DOCUMENTS

| 4,728,775 A | 3/1988 | Van Straten |
| 7,914,162 B1 | 3/2011 | Huang |
| 2009/0191566 A1 | 7/2009 | McKernan et al. |

FOREIGN PATENT DOCUMENTS

| WO | 90/06044 A2 | 6/1990 |
| WO | 2016/040476 A1 | 3/2016 |
| WO | 2019/104337 A1 | 5/2019 |

OTHER PUBLICATIONS

Tam et al., "An Examination of Critical Parameters in Hybridization-Based Epigenotyping Using Magnetic Microparticles," Biotechnol. Prog. 2018, 34:1589-1595. (Year: 2018).*
Karrer et al., "In situ isolation of mRNA from individual plant cells: Creation of cell-specific cDNA libraries," Proc. Natl. Acad. Sci. USA 1995, 92:3814-3818. (Year: 1995).*
Ambion, 2012, Dynabeads Oligo (dT)25, 1-2 pages.
Deangelis, 1995, Solid-Phase Reversible Immobilization for the Isolation of PCR Products, Nucleic Acids Research, Oxford Univesity Press, 23(22);4742-4743.
European Search Report and Written Opinion issued in European Application No. 21155077.7, dated Jul. 12, 2021, 11 pages.
Karrer, 1995, In Situ Isolation of mRNA from Individual Plant Cells: Creation of Cell-Specific CDNA Libraries, Proceedings of the National Academy of Sciences, National Academy of Sciences, 92:3814-3818.
Lambert, 1993, CDNA Library Construction from Small Amounts of RNA Using Paramangnetic Beads and PCR, Nucleic Acids Reseach, Oxford University Press, 21(3):775-776.
Raineri, 1991, Improved Efficiency for Single-Sided PCR by Creating a Reusable Pool of First-Strand CDNA Coupled to a Solid Phase, Nucleic Acids Research, Oxford University Press, 19(14):4010, 1 page.

* cited by examiner

*Primary Examiner* — Kaijiang Zhang
(74) *Attorney, Agent, or Firm* — Brown Rudnick LLP; Adam M. Schoen

(57) ABSTRACT

The present invention provides methods for repurposing beads and other solid supports for separately capturing RNA and DNA without a loss of binding capacity by using a surfactant.

10 Claims, 2 Drawing Sheets

REPURPOSING BEADS IN SAMPLE CLEANUP

FIELD OF THE INVENTION

The invention relates to methods for capturing nucleic acids.

BACKGROUND

Methods of DNA and RNA identification and analysis have become commonplace. Before analysis, nucleic acids frequently must be isolated or captured from the complex mixtures from which they are prepared. Isolation of mRNA, for example, is an important step in the analysis of gene expression and gene regulation and can be invaluable in early disease detection and drug development.

Common methods for DNA and RNA capture employ a magnetic solid support, such as magnetic beads. These methods bind DNA or RNA to the bead through the use one or more ligands on its surface. A variety of ligands are available with an affinity for specific particles. For example, mRNA is frequently captured using beads coated with ligands that have an affinity for the homopolymer of adenosine (poly(A)+ tail) at one end of the mRNA molecule. One such bead for mRNA capture is coated with a homopolymer of deoxythymidine (oligo dT). Once mRNA is captured on the magnetic beads the beads can be collected, unbound material can be removed, the mRNA can be released, cDNA can be synthesized from the RNA, and the cDNA can then analyzed.

Unfortunately, once used for capturing a particular nucleic acid, a solid support may begin to significantly lose its binding capacity over time. Accordingly, once mRNA is captured, released, and cDNA synthesized, a new set of beads must then be employed to capture the cDNA. Utilizing two different sets of beads in this manner limits automation of RNA and DNA analysis and greatly increases the costs associated with early disease detection and drug development. This leaves millions of people afflicted with treatable diseases unable to receive adequate treatment.

SUMMARY OF THE INVENTION

The present invention provides methods for repurposing beads and other solid supports for capturing RNA and DNA without a significant loss of binding capacity. This allows for a single set of beads to be reused to capture both RNA and DNA, and allows for simplified automation of RNA and DNA analysis. This greatly decreases the costs associated with RNA and DNA analysis, early disease detection, and drug development, ensuring that such analysis can be used to drive therapeutic choice.

The invention achieves repurposing of beads and solid supports through the use of a surfactant. For example, RNA and DNA can be captured using a single solid support by first capturing RNA on a solid support coated with an oligo dT, the captured RNA can then be released, and DNA then be captured on the solid support in the presence of surfactant without a loss of binding capacity. The surfactant can be sodium dodecyl sulfate (SDS). Advantageously, the solid support used may be a bead, such as a magnetic bead.

A particular advantage of the present invention is its use in mRNA sequencing. For example, once mRNA is captured, the captured RNA can then be released and cDNA synthesized from the released RNA. The cDNA synthesized from the RNA can then be captured utilizing the same beads. The captured DNA can then be analyzed, for example through sequencing. The use of a single set of beads allows for the nucleic acid analysis to be performed automatically by a device without continuous user input.

DETAILED DESCRIPTION

Figure 1:
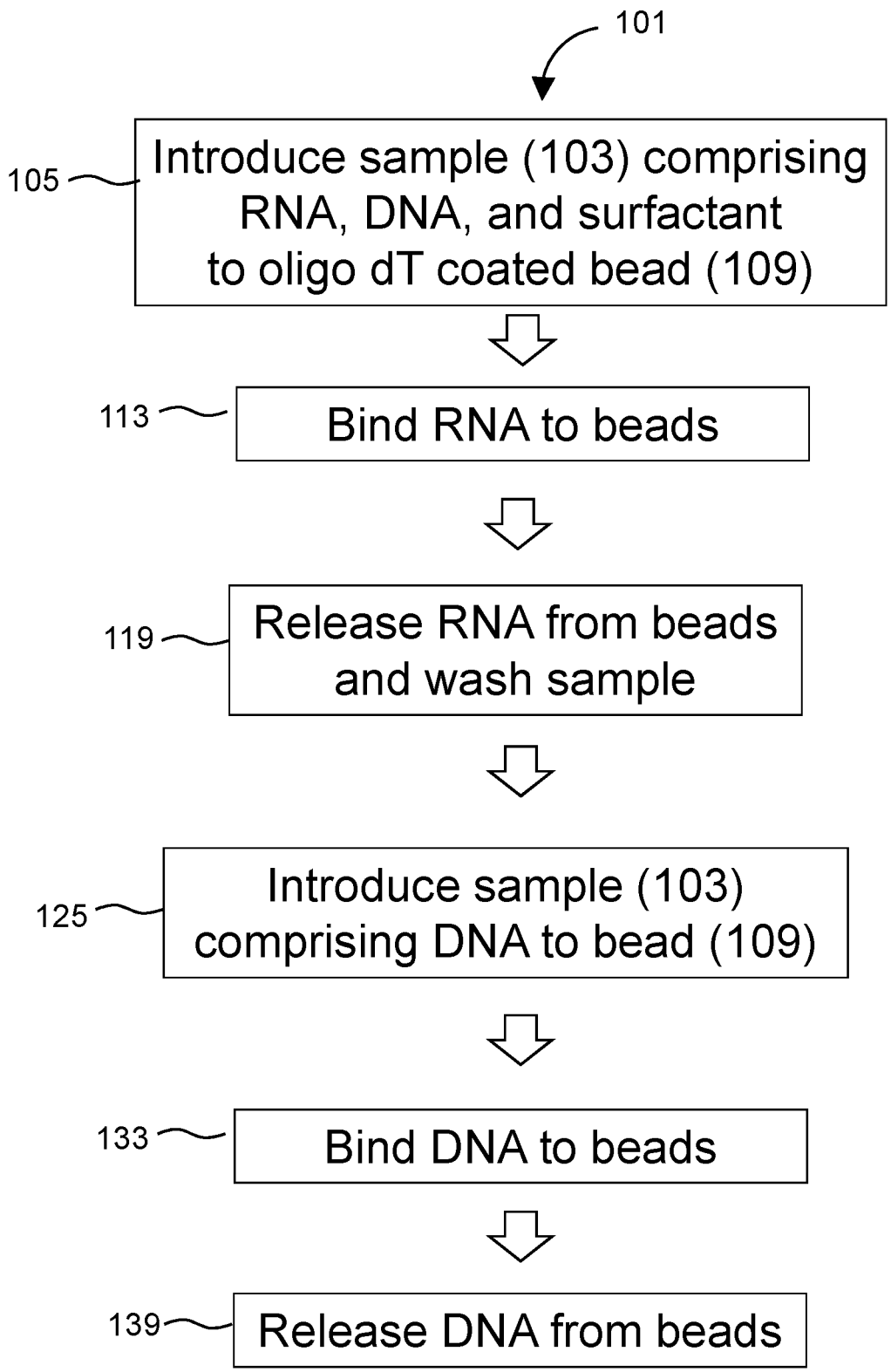
FIG. 1 diagrams a method of repurposing beads for capturing RNA and DNA.

The present invention provides methods for repurposing beads and other solid supports for separately capturing RNA and DNA without a loss of binding capacity by using a surfactant. Functionalized beads and their corresponding buffers used in nucleic acid selection and/or clean up applications are surface treated to carry out specific roles. In the multi-step enzymatic processes it is common practice to change buffers and reaction components to specifically satisfy the needs of different enzymes. This is frequently done by binding the nucleic acid to a solid support and removing components that did not bind. Magnetic beads are the most common support, with one such bead coated with a homopolymer of deoxythymidine (oligo dT). This bead is used to capture messenger RNA molecules (mRNA) that have a homopolymer of adenosine on one end (poly A tail). The nucleic acid can be bound, beads collected, the solution containing unbound materials removed, and nucleic acid resuspended in fresh solution.

In the present invention, by using a surfactant, these beads are initially used to capture and enrich for RNA, such as mRNA, and then reconditioned in a different solution for general purpose DNA binding. The surfactant can be provided to the solid support in the sample containing the RNA and/or the DNA.

The present invention allows for oligo dT coated beads for the more general purpose of binding and purifying double stranded DNA without preference to DNA sequence. By enabling a single bead type to perform two different functions, the method is capable of performing RNA isolation and analysis at a lower cost. The oligo dT beads can be used for the general purpose of DNA isolation without a significant decrease in the beads' DNA binding capacity with reuse. Without being limited to a single theory, it had previously been thought that molecules were interacting with the oligo dT on the surface of the beads in a manner not reversible with normal processing. By the present invention it was determined that pretreatment of the sample to be bound with small quantities of a surfactant, for example SDS, minimized or eliminated the irreversible fouling of the surface.

Use of detergents with oligo dT beads had previously been used to enhance the selectivity of beads for poly A containing fragments, but were not able to minimize or eliminate surface fouling for subsequent DNA capture. Rather, it had previously been necessary to use two different types of beads for RNA and DNA capture and to replace these beads after each use, for example by using oligo dT coated beads for RNA capture and replacing these beads with SPRI beads for DNA capture. By the present invention, under different buffer conditions, it was discovered that SDS generally increases binding efficiency for all nucleic acid species. Accordingly, the present invention allows for the use of these beads as a direct replacement for more typical SPRI beads in DNA isolation. This further enables the use of a single bead type, where the beads under some buffer conditions are used to select/enrich for poly A containing RNA species and successively, under different buffer and binding conditions, to bind double stranded DNA.

Throughout the capture methods of the invention including in nucleic acid capture and elution as well as washing and bead reconditioning steps, a low-ionic strength buffer may be used. Low-ionic strength generally refers to a solution containing less than 50 mM salt (e.g., NaCL) and preferably less than 10 mM or no additional salt beyond the ions present in the buffer itself. Exemplary low-ionic strength solutions may comprise one or more of 10 mM or less Tris-Cl, 0.1 mM or less EDTA, or 4 mM or less $MgCl_2$.

Nucleic acids captured by the methods of the present invention may be from any sample material, for example biological samples. Biological samples may contain viral or cellular material, for example prokaryotic cells and eukaryotic cells. Biological samples may comprise non-mammalian cells or mammalian cells, such as human cells. The nucleic acids may also be from a sample that has undergone one or more processing steps, such as PCR and/or nucleic acid isolation.

The methods of the present invention may be performed in any known composition for RNA and DNA capture, respectively. The components of the composition may be added as a single solution to the sample or components of the composition may be added separately to the sample and/or solid support. When first capturing RNA, the sample composition may comprise a surfactant. The composition may further comprise a crowding agent, such as polyethylene glycol (PEG) and/or salt.

RNA and DNA may be released from beads utilizing one or more washing steps. Any known washing buffer may be used. RNA and DNA may also be released by heating the beads and/or nucleic acids. The surfactant utilized for repurposing beads may be any known surfactant. Advantageously the surfactant may be an anionic detergent, for example sodium dodecyl sulphate (SDS) or other alkali metal alkylsulphate salts.

The solid support may be any known solid support that can be coated with oligo dT and that has an affinity for DNA. For example, advantageously the solid support may have a functional surface that is weakly or strongly positively charged or hydrophobic. The solid support may be a bead, particle, sheet, gel, filter, capillary, tube, plate, or well. The solid support may be magnetic or paramagnetic. Magnetic solid supports provide the advantage of being easily separated using a magnetic field without the need to utilize more strenuous methods, such as centrifugation. For example, the solid support may be a paramagnetic bead made of polystyrene surrounded by a layer of magnetite and/or carboxyl molecules, such as beads with a similar surface characteristic to SPRI beads. SPRI beads may be as described in Deangelis et al. (1995) "Solid-phase reversible immobilization for the isolation of PCR products", Nucleic Acids Res. 23(22):4742-3, incorporated by reference.

RNA and DNA can be captured using a single solid support by first capturing RNA on a solid support coated with an oligo dT in the presence of a surfactant, the captured RNA can then be released, and DNA an then be captured on the solid support without a loss of binding capacity. The surfactant can be sodium dodecyl sulfate (SDS). Advantageously, the solid support used may be a bead, such as a magnetic bead.

FIG. 1 diagrams an exemplary method for repurposing beads to separately capture RNA and DNA from a single sample. A sample 103 comprising RNA, DNA, and a surfactant, for example SDS, is introduced to oligo dT coated beads 109. RNA from the sample is bound to the oligo dT coated beads based on the affinity for RNA poly A tailing by the oligo dT. The beads are separated from the sample and RNA is released from the beads. The sample 103, now free of RNA, is then reintroduced to the beads 109 and DNA is bound to the beads, for example through charge interactions between the bead and the DNA. The DNA is then released from the beads and each of the RNA and DNA can be analyzed.

Figure 2:
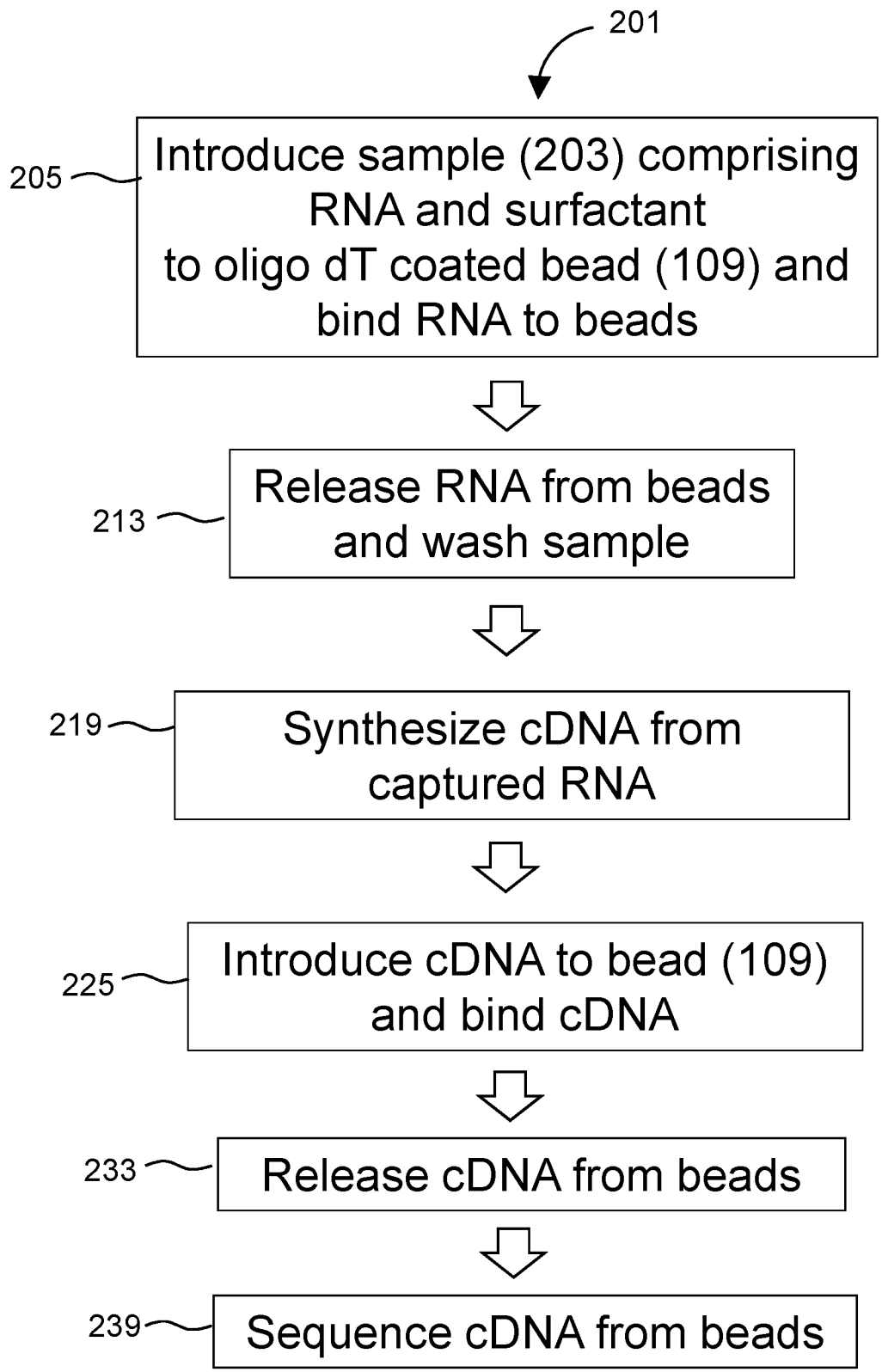
FIG. 2 diagrams a method of repurposing beads for capturing RNA and synthesized cDNA.

FIG. 2 diagrams an exemplary method for repurposing beads to capture cDNA synthesized from RNA in a sample. A sample 203 comprising RNA and a surfactant, for example SDS, is introduced to oligo dT coated beads 109. RNA from the sample is bound to the oligo dT coated beads based on the affinity for RNA poly A tailing by the oligo dT. The beads are separated from the sample and RNA is released from the beads. cDNA is then synthesized from the RNA and introduced into a new sample. The cDNA sample is mixed with a binding buffer containing SDS, then introduced to the beads 109 and cDNA is bound to the beads. The cDNA is then released from the beads and the cDNA can be analyzed, for example by sequencing.

cDNA can be synthesized from RNA by any known method. For example, in an advantageous embodiment cDNA synthesis may be primed with oligo dT and cDNA synthesis may occur on the bead prior to releasing the RNA. DNA may also be sequenced by any known method, such as by using next generation sequencing (NGS) platforms. DNA may be amplified prior to analysis, for example by PCR. DNA may amplified while still bound to the solid support.

By utilizing a single solid support or set of beads, the invention allows isolation of RNA and DNA to be performed automatically by a device without user input or the need to input new beads with each isolation. For example, the beads may be within a device. Accordingly, once the sample 103 or 203 is introduced 105 or 205 into the device, the device may automatically proceed through the method of 101 or 201 without input from the user or with limited input from the user. The methods of the present invention may be performed by a device without significant input from a user, for example with a single user input to isolate and sequence RNA from a sample provided to the device, further reducing the costs associated with nucleic acid isolation.

EXAMPLES

Example 1: Bench Top Method

RNA-Seq libraries were generated where all purification steps were performed with a single set of oligo dT magnetic beads (GE Health Care, Ser-Mag oligo dT beads). 100 ng of total RNA derived from K562 cell line was mixed with 35 µl of Oligo dT beads as recommended by the supplier. Following annealing the beads were pulled to the side of the tube and the solution containing any unbound RNA discarded. The beads were re-suspended and washed as recommended by the supplier. The beads were collected and the wash buffer was discarded. The bound RNA was eluted in 20 µl of RNA Fragmentation buffer (Tecan Group Ltd., Universal RNA-Seq) and incubated at 94° C. for 7 minutes as recommended. The beads were collected and the fragmented RNA transferred to a fresh tube.

The oligo dT beads were re-suspended in 40 ul of a reconditioning solution (Bead Bind Buffer) containing 21% PEG 4000, 2.5M NaCl, 50 mM Tris, 0.1mMEDTA and 0.03% SDS.

A Reverse Transcriptase master mix solution (5 μl) from a Universal RNA-Seq kit (Tecan Group Ltd.) was added to the fragmented RNA, mixed and incubated at 25° C. for 5 minutes, 42° C. for 15 minutes, and 70° C. for 15 minutes as recommended. Following incubation, 50 μl of Second Strand maser mix (Tecan Group Ltd., Universal RNA-Seq) was added, mixed and incubated at 16° C. for 60 minutes. The reaction mixture was not heat denatured but simply mixed with the reconditioned oligo dT beads (above). The beads were incubated at room temperature, collected and the solution discarded. These beads were rinsed with 180 ul of a Bead Wash solution containing 13% PEG 8000, 50 mM LiCl, 50 mM Tris, 0.1 mM EDTA and 0.01% Tween 20. Following the wash, the ds cDNA was eluted from the beads in 20 ul 10 mM Tris, 1 mM EDTA and transferred to a fresh tube.

The beads were re-suspended in 50 ul of the reconditioning buffer (Bead Bind buffer) described above and held at room temperature until required.

Ligation master mix including sequencing adapters (Tecan Group Ltd., Universal RNA-Seq) was added to the ds cDNA and incubated as recommended by supplier. Following ligation, the reaction mixture was directly added to the reconditioned oligo dT beads, mixed and held at room temperature. The beads were washed (Bead Wash solution) and DNA eluted in 20 μl 10 mM Tris, 0.1 mM EDTA. The eluted DNA was transferred to a fresh tube where strand selection and PCR amplification (17 cycle) were performed as recommended.

The oligo dT beads were re-suspended as before in 50 μl Bead Bind buffer.

Following amplification, the reaction mixture was mixed with the beads, held at room temperature, collected and rinsed as previously described. The DNA libraries were eluted from the beads in 30 μl TE buffer, quantitated and fragment length distribution determined (Fragment Analyzer, Agilent Technologies). Yields (~300 ng) and fragment length distribution were consistent with that typically achieved when fresh SPRI beads were used in each DNA purification step. These libraries were diluted and sequenced (MiSeq, Illumina). Analysis of the sequencing data verified that the number of genes detected was consistent with prior experience when fresh SPRI beads were used in each DNA purification step, thereby validating the suitability of the bead-reuse methods of the invention.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

The invention claimed is:

1. A method for capturing RNA and DNA using a solid support, the method comprising:
   capturing mRNA on a solid support coated with an oligo dT in a low ionic strength buffer;
   releasing the captured mRNA;
   synthesizing cDNA from the released mRNA, and
   adding surfactant, salt and a crowding agent then capturing cDNA synthesized from the mRNA on the solid support.

2. The method of claim 1, wherein the surfactant is sodium dodecyl sulfate (SDS).

3. The method of claim 2, wherein the solid support is a bead.

4. The method of claim 3, wherein the bead is a magnetic bead.

5. The method of claim 1, further comprising the step of sequencing the DNA.

6. The method of claim 5, wherein the method is performed automatically by a device without user input.

7. A method for capturing nucleic acids on a solid support, the method comprising:
   repeatedly capturing and releasing nucleic acids on a solid support without denaturing or removing proteins between captures; and
   introducing surfactant to a sample comprising the nucleic acids before capture, wherein the nucleic acids comprise mRNA and cDNA, and wherein the cDNA is synthesized from the mRNA between captures.

8. The method of claim 7, wherein the surfactant is sodium dodecyl sulfate (SDS).

9. The method of claim 7, wherein the solid support is a bead.

10. The method of claim 9, wherein the bead is a magnetic bead.

* * * * *